US010926102B2

(12) United States Patent
DiMauro (10) Patent No.: US 10,926,102 B2
(45) Date of Patent: Feb. 23, 2021

(54) TRANSORBITAL NIR LIGHT THERAPY DEVICES

(71) Applicant: Janssen Pharmaceutica NV, Beerse (BE)

(72) Inventor: Thomas M DiMauro, Southboro, MA (US)

(73) Assignee: Janssen Pharmaceutica NV, Beerse (BE)

( * ) Notice: Subject to any disclaimer, the term of this patent is extended or adjusted under 35 U.S.C. 154(b) by 0 days.

(21) Appl. No.: 16/419,369

(22) Filed: May 22, 2019

(65) Prior Publication Data

US 2020/0324140 A1 Oct. 15, 2020

Related U.S. Application Data

(60) Provisional application No. 62/834,394, filed on Apr. 15, 2019, provisional application No. 62/844,855, filed on May 8, 2019.

(51) Int. Cl.
*A61N 5/06* (2006.01)

(52) U.S. Cl.
CPC .... *A61N 5/0622* (2013.01); *A61N 2005/0648* (2013.01); *A61N 2005/0651* (2013.01); *A61N 2005/0659* (2013.01); *A61N 2005/0662* (2013.01)

(58) Field of Classification Search
CPC ................ A61N 5/0622; A61N 2005/0648
USPC ........................................... 607/88
See application file for complete search history.

(56) References Cited

U.S. PATENT DOCUMENTS

| 4,283,127 | A | 8/1981 | Rosenwinkel et al. |
|---|---|---|---|
| 6,350,275 | B1 | 2/2002 | Vreman et al. |
| 6,559,096 | B1 | 5/2003 | Smith |
| 6,688,132 | B2 | 2/2004 | Smith |
| 6,701,724 | B2 | 3/2004 | Smith |
| 6,857,739 | B1 | 2/2005 | Watson |
| 6,968,711 | B2 | 11/2005 | Smith |
| 8,167,920 | B2 | 5/2012 | DiMauro |
| 8,734,498 | B2 | 5/2014 | DiMauro et al. |
| 9,470,908 | B1 | 10/2016 | Frankel et al. |
| 10,561,857 | B2 | 2/2020 | Toselli |
| 2001/0028431 | A1 | 10/2001 | Rossin |
| 2004/0215293 | A1 | 10/2004 | Eells et al. |
| 2005/0278003 | A1 | 12/2005 | Feldman |
| 2006/0136018 | A1 | 6/2006 | Lack et al. |
| 2006/0198128 | A1* | 9/2006 | Piepgras ............ B29C 39/10 362/147 |
| 2006/0259100 | A1 | 11/2006 | Hilburg |
| 2007/0195515 | A1 | 8/2007 | Waters |

(Continued)

OTHER PUBLICATIONS

Bozkurt, "Safety Assessment of Near Infrared Light Emitting Diodes for Diffuse Optical Measurments", Biomedical Engineering OnLine, 2004, 3:9, 10 pages.

(Continued)

*Primary Examiner* — Gary Jackson
*Assistant Examiner* — Zahed Kabir (57) ABSTRACT

An NIR light emitting device has a flat NIR light emitter attached to a distal end of a heat pipe on its lower side and an optically-transparent, thermal insulator on its upper side. The proximal end of the heat pipe is thermally connected to a cooling element. The light emitter is connected to a power source to irradiate NIR light.

9 Claims, 11 Drawing Sheets

(56) References Cited

U.S. PATENT DOCUMENTS

| | | |
|---|---|---|
| 2007/0233207 A1 | 10/2007 | Poirrier et al. |
| 2008/0062682 A1 | 3/2008 | Hoelen |
| 2008/0193664 A1 | 8/2008 | Gonzalez et al. |
| 2008/0233053 A1 | 9/2008 | Gross et al. |
| 2008/0262575 A1 | 10/2008 | Aunio |
| 2010/0004499 A1 | 1/2010 | Brigatti |
| 2010/0324631 A1 | 12/2010 | Tass |
| 2011/0060266 A1* | 3/2011 | Streeter ............... A61N 5/0613 604/20 |
| 2011/0077548 A1 | 3/2011 | Torch |
| 2011/0181832 A1 | 7/2011 | Smith et al. |
| 2011/0295345 A1 | 12/2011 | Wells |
| 2011/0319878 A1 | 12/2011 | DiMauro et al. |
| 2012/0215291 A1 | 8/2012 | Pugh et al. |
| 2013/0066404 A1 | 3/2013 | Tapper et al. |
| 2013/0201285 A1 | 8/2013 | Mao et al. |
| 2014/0313716 A1* | 10/2014 | Lang ...................... H01L 35/30 362/235 |
| 2014/0330129 A1 | 11/2014 | Grenon et al. |
| 2014/0358199 A1 | 12/2014 | Lim |
| 2014/0376232 A1* | 12/2014 | Behr ......................... F21V 7/06 362/294 |
| 2015/0005750 A1 | 1/2015 | Kelleher et al. |
| 2016/0106950 A1 | 4/2016 | Vasapollo |
| 2016/0263395 A1* | 9/2016 | Siegel .................. A61B 5/4836 |
| 2016/0342206 A1 | 11/2016 | Shazly et al. |
| 2017/0087017 A1 | 3/2017 | Iseli |
| 2017/0296051 A1 | 10/2017 | Kislinger |
| 2018/0021032 A1* | 1/2018 | DiMauro ............. A61B 17/025 600/202 |
| 2018/0104514 A1 | 4/2018 | Gertner et al. |
| 2018/0188556 A1 | 7/2018 | Portney |
| 2018/0193364 A1 | 7/2018 | DiMauro et al. |
| 2018/0264284 A1* | 9/2018 | Alvarez ............... A61N 5/0622 |
| 2019/0106543 A1 | 4/2019 | Chintapalli et al. |

OTHER PUBLICATIONS

Radian Thermal Products, "White Paper: Heat Pipes & Vapor Chambers", Nov. 2014, 9 pages, www.radiantheatsinks.com.

[No Author Listed]—"Point-of-care Concussion Therapy", Office for Technology Commercialization, University of Minnesota—Driven to Discover, Technology #20180342, 2018, Regents of the University of Minnesota, 3 pages.

[No Author Listed]—"Vielight: The Future of Brain Photobiomodulation", https://vielight.com/brain-photobiomodulation-devices/, Vielight, Inc., accessed Jan. 10, 2020, 11 pages.

[No Author Listed]—"MedX Health for Concussions: Rehab Laser Console System", https://medxhealth.com/en/product-rehab-console/, accessed Jan. 20, 2020, 4 pages.

Anders, et al.—"Light Supports Neurite Outgrowth of Human Neural Progenitor Cells In Vitro: The Role of P2Y Receptors", IEEE, Journal of Selected Topics in Quantum Electronics, Jan.-Feb. 2008, vol. 14 Issue 1, pp. 118-125.

Aurora CTS, Aurora Concussion Therapy Systems, Inc.—"Helping the brain heal faster", Home Page http://aurora-cts.com/, accessed Jan. 10, 2020, 1 page.

Bartels, et al.—"The neural correlates of maternal and romantic love", NeuroImage, Mar. 2004, vol. 21, Issue 3, pp. 1155-1166, by Elsevier.

Blanco, et al.—"Improving executive function using transcranial infrared laser stimulation", Journal of Neuropsychology, Nov. 28, 2016, published in final form Mar. 2017, vol. 11, Issue 1, pp. 14-25.

Bozkurt, "Safety Assessment of Near Infrared Light Emitting Diodes for Diffuse Optical Measurements", Biomedical Engineering OnLine, 2004, 3:9, 10 pages.

Byrnes, "Light Promotes Regeneration and Functional Recovery and Alters the Immune Response After Spinal Cord Injury", Lasers Surg. Medicine, 2005, 9999, pp. 1-15.

Byrnes, "Light promotes regeneration and functional recovery and alters the immune response after spinal cord injury", Lasers Surgery Medicine, Mar. 2005, 36(3) 171-85, [Abstract].

Byrnes, "Low Power Laser Irradiation Alters Gene Expression of Olfactory Ensheathing Cells in Vitro", Lasers Surg Med., Aug. 2005, vol. 37, issue 2, pp. 161-71, (Abstract).

Cassano et al., "Near-Infrared Transcranial Radiation for Major Depressive Disorder: Proof of Concept Study", Psychiatry J. 2015, 352979, pp. 1-8.

Cho, "Effect of Low-level Laser Therapy on Osteoarthropathy in Rabbig", In Vivo, Sep.-Oct. 2004, vol. 18, Issue 5, pp. 585-591.

Dimauro et al.—"Project Pleasant: Transorbital Near infrared Light Therapy for the Orbitofrontal Cortex of the Injured Brain", MIT write-up, May 19, 2019, 2 pages.

Fahim, "Orbitofrontal dysfunction in a monozygotic twin discordant for postpartum affective psychosis: a functional magnetic resonance imaging study", Bipolar Disorders 2007, vol. 9, pp. 541545.

Geneva, "Photobiomodulation for the treatment of retinal diseases: a review", Int. J. Ophthalmol., Jan. 18, 2016, vol. 9, Issue 1, pp. 145-152.

Gorbatenkova, "Reactivation of superoxide dismutase by the helium-neon laser irradiation", Biofizika, Jul.-Aug. 1988, vol. 33, Issue 4, pp. 717-9 (Abstract).

Hamblin—"Shining light on the head: Photobiomodulation for brain disorders", BBA Clinical, vol. 6 (2016), Oct. 1, 2016, pp. 113-124, published by Elsevier B.V.

International Searching Authority—International Search Report and Written Opinion for International Application No. PCT/US2018/013081, dated Apr. 5, 2018, 9 pages.

Kamanli—"Plasma lipid peroxidation and antioxidant levels in patients with rheumatoid arthritis", Cell Biochemistry and Function, 2004, vol. 22, pp. 53-57.

Karu, "Suppression of Human Blood Chemiluminescence by Diode Laser Irradiation At Wavelengths 660, 820, 880 or 950 nm", Laser Therapy, Feb. 27, 1993, vol. 5, pp. 103-109.

Keedy, "An overview of intracranial aneurysms", McGill Journal of Medicine, 2006, vol. 9, Issue 2, pp. 141-146.

King, "Doing the right thing: A common neural circuit for appropriate violent or compassionate behavior", NeuroImage, 2006, vol. 30, pp. 1069-76.

Kringelbach, "A Specific and Rapid Neural Signature for Parental Instinct", PLoS One, 2008, Feb. 27, 2008, vol. 3, Issue 2, e1664, pp. 1-7.

Kroczek, "Prefrontal functional connectivity measured with near-infrared spectroscopy during smoking cue exposure", Addiction Biology, 2015, vol. 22, Issue 2, 2 pages (Abstract).

Leibenluft, "Mothers' neural activation in response to pictures of their children and other children", Biololgy Psychiatry, Aug. 15, 2004, vol. 56, Issue 4, pp. 225-232 (Abstract).

Lenzi, "Neural basis of maternal communication and emotional expression processing during infant preverbal stage", Cereb Cortex, May 2009, vol. 19, Issue 5, pp. 1124-1133.

Leon-Carrion, "Functional Near-infrared Spectroscopy (fNIRS): Principles and Neuroscientific Applications", Neuroimaoino—Methods, Prof. Peter Bright (Ed.), 2012, ISBN:978-953-51-0097-3, In Tech, pp. 47-74.

Leung, Treatment of Experimentally Induced Transient Cerebral Ischemia With Low Energy Laser Inhibits Nitric Oxide Synthase Activity and Up-Regulates the Expression of Transforming Growth Factor-Beta 1, Laser Suro. Med., 2002, vol. 31, pp. 283-288.

Liang, "Photobiomodulation partially rescues visual cortical neurons from cyanide-induced apoptosis", Neuroscience., May 12, 2006; vol. 139, Issue 2, pp. 639-49.

Lim, "Inventor's Notes on Whole Brain Photobiomodulation with Vielight Neuro—a Transcranial-Intranasal Light Therapy Combination", Jan. 2016, pp. 8 and 16).

Lim, "The Potential Of Intranasal Light Therapy For Brain Stimulation", Presented at the NAALT Conference, Palm Beach Gardens, Florida, Feb. 2, 2013, pp. 1-16.

Manji, "Impairments of Neuroplasticity and Cellular Resilience in Severe Mood Disorders: Implications for the Development of Novel Therapeutics", Psychopharmacol Bull., 2001 Spring, vol. 35, Issue 2, pp. 5-49 (Abstract).

(56) References Cited

OTHER PUBLICATIONS

Merry, "Treatment of dry Age-related Macular Degeneration with Photobiomodulation", presented at ARVO, Fort Lauderdale, FL, May 7, 2012.
Minagawa-Kawai, "Prefrontal activation associated with social attachment: Facial-emotion recognition in mothers and infants", Cerebral Cortex, Feb. 2009, vol. 19, pp. 284-292 (Abstract).
Moch Izuki-Oda, "Effects of near-infra-red laser irradiation on adenosine diphosphate contents of rat brain tissue", Neurosci. Letters (2002), vol. 323, pp. 208-210.
Moses-Kolks, "Serotonin 1A receptor reductions in postpartum depression: a PET study", Fertil. Steril., Mar. 2008 vol. 89, Issue 3, pp. 685-92.
Naeser et al., "Significant Improvements in Cognitive Performance Post-Transcranial, Red/Near-Infrared Light-Emitting Diode Treatments in Chronic, Mild Traumatic Brain Injury: Open-Protocol Study", J. Neurotrauma 2014, vol. 31, Issue 11, pp. 1008-1017.
Neumeister, "Effects of tryptophan depletion on serum levels of brain-derived neurotrophic factor in unmedicated patients with remitted depression and healthy subjects", Am J Psychiatry, Apr. 2005, vol. 162, Issue 4, pp. 805-7, (Abstract).
Nitschke, "Orbitofrontal cortex tracks positive mood in mothers viewing picturesof their newborn infants", Neurolmaoe 21 (2004) 583-592.
Noriuchi, "The Functional Neuroanatomy of Maternal Love: Mother's Response to Infant's Attachment Behaviors" Biol. Psychitary, Feb. 15, 2008, vol. 63, Issue 4, pp. 415-423, (Abstract).
Oron, "Ga-As (808 nm) Laser Irradiation Enhances ATP Production in Human Neuronal Cells in Culture", Photomed Laser Surg., Jun. 2007, vol. 25, Issue 3, pp. 180-2 (Abstract).
Ostrakhovich, "Active Form of Oxygen and Nitrogen in Blood Cells of Patients with Rheumatoid Arthritis: Effect of Laser Therapy", Vestn Ross Akad Med Nauk., 2001, vol. 5, pp. 23-7 (Abstract).
Ranote, "The neural basis of maternal responsiveness to infants: an fMRI study", Neuroreport, Aug. 6, 2004; vol. 15, Issue 11, pp. 1825-9, (Abstract).
Rochkind, "Increase of neuronal sprouting and migration using 780 nm laser phototherapy as procedure for cell therapy", Lasers Surq. Med., 2009, vol. 41, pp. 277-281 (Abstract).
Roelofs, "On the neural control of social emotional behavior", SCAN (2009) vol. 4, pp. 50-58.
Romm, "Action of laser radiation on the peroxide chemiluminescence of wound exudate", Biull. Eksp. Biol. Med. Oct. 1986 vol. 102, Issue 10, pp. 426-8 (Abstract).
Salehpour et al.—"Brain Photobiomodulation Therapy: a Narrative Review", Molecular Neurobiol (2018) vol. 55, Issue 8, pp. 6601-6636, Published online Jan. 11, 2018, Springer Science-Business Media, LLC, part of Springer Nature 2018.
Schiffer, "Psychological benefits 2 and 4 weeks after a single treatment with near infrared light to the forehead: a pilot study of 10 patients with major depression and anxiety", Behavioral and Brain Function, Dec. 8, 2009 , vol. 5:46, 13 pages.
Seifritz, "Differential sex-independent amygdala response to infant crying and laughing in parents versus nonparents", Biol. Psychiatry, 2003, vol. 54, pp. 1367-75.
Tang, "Photobiomodulation in the treatment of patients with noncenter-involving diabetic macular oedema", Br. J. Ophthalmol., Aug. 2014, vol. 98, Issue 8, pp. 1013-1015.
Tedford, "Quantitative analysis of transcranial and intraparenchymal light penetration in human cadaver brain tissue", Lasers in Surgery and Medicine 2015, vol. 47, pp. 312-322. (Abstract).
Uozumi et al.—"Targeted Increase in Cerebral Blood Flow by Transcranial Near-Infrared Laser Irradiation", Lasers in Surgery and Medicine, vol. 42, Issue 6, Aug. 2010, pp. 566-576, Published by ResearchGate.
Vladimirov, "Photobiological Principles of Therapeutic Applications of Laser Radiation Biochemistry", 2004, vol. 69, Issue 1, pp. 81-90, Moscow.
Vladimirov, "Photoreactivation of Superoxide Dismutase by Intensive Red (Laser)Light", Free Rad. Biol. Med., 1988, vol. 5, Issues 5-6, pp. 281-6.
Volotovskaia, "Antioxidant action and therapeutic efficacy of laser irradiation of blood in patients with ischemic heart disease", Vopr Kurortol Zizioter Lech Fiz Kult May-Jun. 2003 vol. 3, pp. 22-5 (Abstract).
Wada, "Lithium: potential therapeutics against acute brain injuries and chronic neurodegenerative diseases", J Pharmacol Sci. Dec. 2005; vol. 99, Issue 4, pp. 307-21 (Abstract).
Wang, "Lithium Inhibition of Protein Kinase C Activation-Induces Serotonin Release", iPsychopharmacoloov (Berl). 1989. vol. 99, Issue 2, pp. 213-8 (Abstract).
Wollman, "In vitro cellular processes sprouting in cortex microexplants of adult rat brains induced by low power laser irradiation", Neurol. Res. 1998, Jul, vol. 20, Issue 5, pp. 470-2 (Abstract).
Wollman, "Low power laser irradiation enhances migration and neurite sprouting of cultured rat embryonal brain cells" Neurol. Res. Oct. 1996, vol. 18, Issue 5, pp. 467-70 (Abstract).
Wong-Riley, "Light-emitting Diode Treatment Reverses the Effect of TTX on Cytochrome Oxidase in Neurons", Neuroreport, 2001, vol. 12, Issue 14, pp. 3033-3037 [Abstract].
Wong-Riley, "Photobiomodulation Directly Benefits Primary Neurons Functionally Inactivated by Toxins", J Biol Chem., Feb. 11, 2005, vol. 280, No. 6, pp. 4761-71.
Yaroslavsky, "Optical properties of selected native and coagulated human brain tissues in vitro in the visible and near infrared spectral range", Biol., 2002, vol. 47, pp. 2059-73.
Zhang, "Low-Power Laser Irradiation Inhibiting $A\beta_{25-35}$- induced PC12 Cell Apoptosis via PKC Activiation" *Cell Physiol Biochem.*, 2008, vol. 22, Issue 1-4, pp. 215-22.
*Frontal Sinus Transillumunation Video, 2010*, https://www.youtube.com/watch?v=8Lo3bENDqzs.
International Searching Authority—International Search Report and Written Opinion for International Application No. PCT/US2020/053510, dated Jul. 27, 2010, 20 pages.
Cassano et al.—"Selective photobiomodulation for emotion regulation: model-based dosimetry study", https://www.spiedigitallibrary.org/journals/neurophotonics/volume-6/issue-1/015004/Selective-photobiomodulation-for-emotion-regulation-model-based-dosimetry-study/10.1117/1.NPh.6.1.015004.full?SSO=1, Neurophotonics SPIE Digital Library, vol. 6, Issue 1, Epub. Feb. 7, 2019, 13 pages.

\* cited by examiner

TRANSORBITAL NIR LIGHT THERAPY DEVICES

CONTINUING DATA

This application claims the benefit of U.S. Ser. No. 62/834,394, entitled "Transorbital NIR Light Therapy Devices" (DiMauro), filed on Apr. 15, 2019 and U.S. Ser. No. 62/844,855, entitled "Transorbital NIR Light Therapy Devices" (DiMauro), filed on May 8, 2019, the specifications of which are hereby incorporated by reference in their entireties.

BACKGROUND OF THE INVENTION

US 2018-0193664 (Janssen) discloses light therapy devices adapted to be placed on the eyelid and inserted between the eyeball and eyesocket in order to provide NIR light therapy to the orbitofrontal cortex. The heat generated by such devices may be a significant concern.

SUMMARY OF THE INVENTION

There have now been developed a) embodiments in which the NIR light emitter having an NIR light emitting diode (LED) is placed directly on the eyelid and cooling means are provided on the device, and b) embodiments in which a light pipe is provided on the eyelid and an light emitter having an NIR LED is placed on the proximal end of the light pipe so that the light emitter does not contact the eyelid but instead is located a substantial distance therefrom.

Therefore, in some embodiments, there is provided an NIR light emitting device comprising:
a) an NIR light emitter having a base having a lower side and an upper side, and an NIR LED attached to the upper side of the base,
b) a thermal insulator,
c) a heat pipe having a distal end portion and a proximal end portion,
d) a cooling element, and
e) a power source,
wherein the distal end portion of the heat pipe is attached to the lower side of the base of the NIR light emitter,
wherein the thermal insulator is attached to the upper side of the base of the NIR light emitter,
wherein the proximal end of the heat pipe is attached to the cooling element, wherein the NIR light emitter is in electrical connection with the power source.

DETAILED DESCRIPTION OF THE INVENTION

Figure 1:
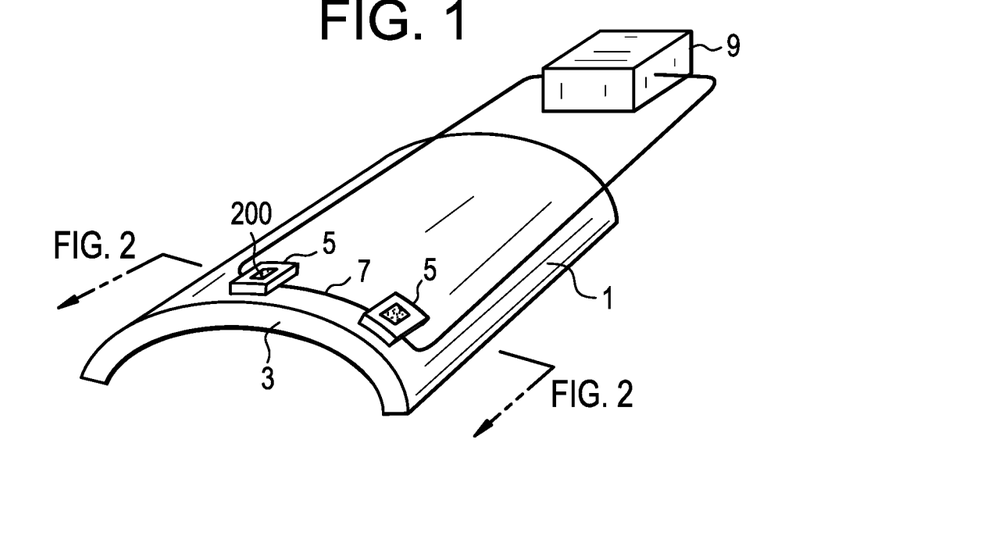
FIG. 1 discloses a perspective view of a device of the present invention having a pair of light emitters attached to a curved based adapted for insertion into the eyesocket.

In some embodiments, and now referring to FIG. 1, there is provided a light delivery device comprising:
a) a base 1 comprising a substantially concavo-convex distal end portion 3, wherein the substantially concavo-convex distal end portion comprises a metallic composition,
b) a plurality of light emitters 5 attached to the convex side 7 of the substantially concavo-convex distal end portion, wherein the light emitter is oriented so that a majority of the light emitted by its LED faces away from the substantially concavo-convex distal end portion,
c) a power source 9 in electrical connection with the plurality of light emitters.

There are two readily-apparent benefits to this embodiment.

Figure 2:
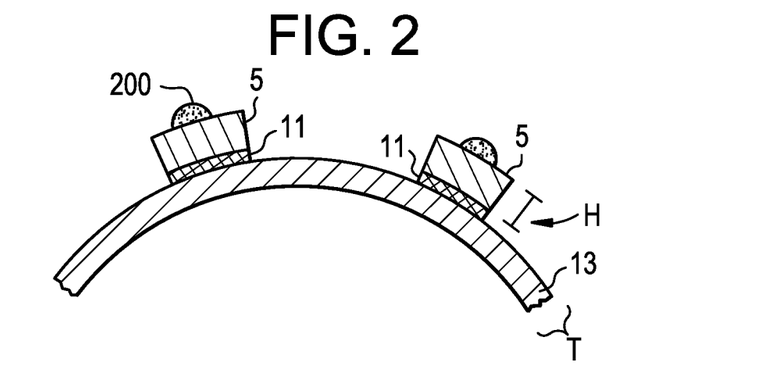
FIG. 2 is a cross section of FIG. 1.

First, the metallic nature of the substantially concavo-convex distal end portion provides for heat dissipation, thereby drawing heat the powered light emitters and reducing the temperature at the eyelid Now referring to FIG. 2, light emitters 5 are attached to a section of aluminum pipe 13 (via a section of very thin, double-sided thermally conductive tape 11 or a metallic paste or braze) and then powered by a 3 Volt battery.

Second, the light emitter is separated from the eyelid by a non-translucent concavo-convex distal end portion of the base. Thus, any light that is emitted by the light emitter towards the brain but then diffracted by tissue back towards the eye will be blocked by the metallic component. This provides a second measure of safety, thereby allowing for higher light fluxes to be used.

Figure 3:
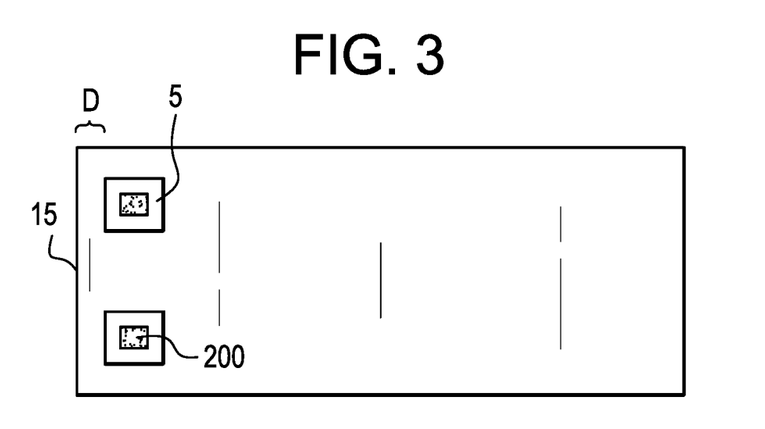
FIG. 3 is an elevation view of a portion of a device of the present invention, showing the light emitters set back from the distal edge of the base.

In some embodiments, and now referring to FIG. 3, the light emitters are situated at a distance D of least 3 mm (preferably at least 5 mm) from the distal end 15 of the concavo-convex portion. In this condition, light must travel over that spacing before reaching the eye, and so that spacing acts as a block of NIR light reaching the eye.

Preferably the substantially concave distal end portion forms an arc of at least about 90 degrees, more preferably at least about 120 degrees, so that light emitter situated at the medial extreme can reach medial OFC structures like the gyrus rectus.

It was found that inserting a substantially concavo-convex element into the region between the eyelid and eyesocket was fairly benign when the thickness of the element was about 1.5 mm, but became uncomfortable when the thickness of the element was about 6 mm. Thus, and now referring back to FIG. 2, preferably, the substantially concavo-convex distal end portion has a thickness T of less than 5 mm, preferably less than 3 mm, more preferably less than 2 mm. Similarly, the light emitters that are disposed on this element should be as short as possible to accommodate the comfort concern. Preferably, such an light emitter has a height H of less than 2 mm, preferably less than 1 mm. In some embodiments, the thin light emitter is the Luxeon Saber Micro-Z1 850 nm light emitter, available from Quadica Developments Inc at luxeonstar.com, Lethbridge, Alberta, Canada, which has a height of about 1 mm and has an irradiance rated at about 1050 mwatts.

Figure 4:
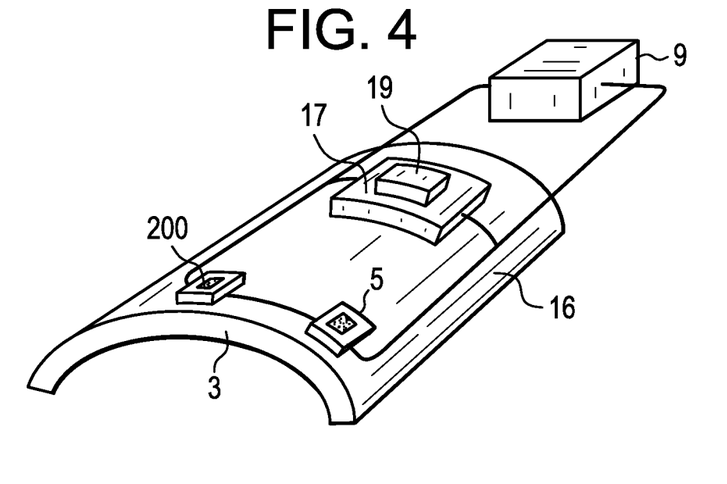
FIG. 4 is a perspective view of a device of the present invention having a thermoelectric cooling unit disposed at a first location.
Figure 5:
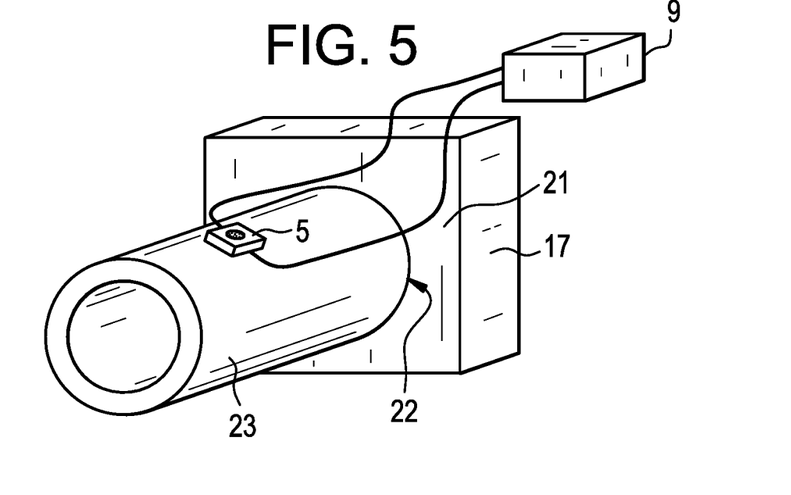
FIG. 5 is a perspective view of a device of the present invention having a thermoelectric cooling unit disposed at a second location.

In some embodiments, and now referring to FIG. 4, the base is metallic and has a proximal portion 16 that carries a thermoelectric cooler 17. The cold side of the thermoelectric cooler is put in contact with the proximal portion of the base and will thereby cool the base when actuated, thereby lessening overheating concerns. Preferably the thermoelectric cooler is attached to the proximal portion of the base by double sided thermally conductive tape, a braze or a metallic paste. Preferably, the proximal portion of the base is substantially flattened to accommodate the flat nature of the conventional thermoelectric cooler. Typically, a heat sink 19 and/or fan is attached to the hot side of the thermoelectric cooler. In other embodiments, as in FIG. 5, the flat cold face 21 of the thermoelectric cooler 17 abuts the annular proximal end face 22 of a tubular base 23.

Figure 6:
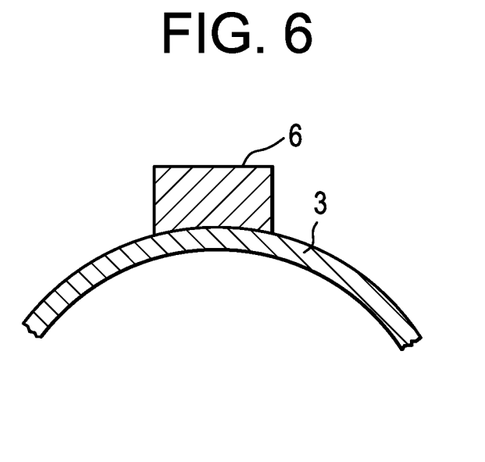
FIG. 6 is a cross section of a device of the present invention in which ice is placed on the base as a cooling source.
Figure 7:
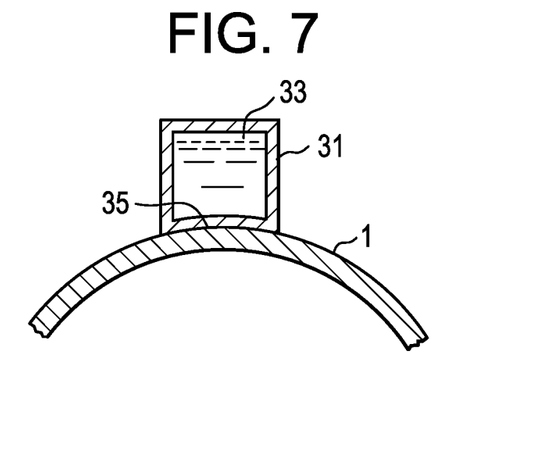
FIG. 7 is a cross-section of a device of the present invention in which a thermally conductive container containing a cooling element is placed on the base as a cooling source.

In some embodiments, and now referring to FIG. 6, ice 29 is placed on the base as a cooling source. In other embodiments, and now referring to FIG. 7, a thermally conductive container 31 containing a cooling element 33 is placed on the base 1 as a cooling source. Preferably, the thermally conductive container comprises a metal skin. Preferably, the cooling element is either ice or a chilled hydrogel. Preferably, the hydrogel comprises sodium polyacrylate. The thermally conductive container is placed in a refrigerator before use so as to cool the cooling element, and is taken out of the refrigerator just prior to use. When the container is placed on the base when the LIGHT EMITTER is energized, the cooling element functions so as to cool the metallic base during use, thereby reducing the temperature of the light emitter through conductive cooling.

Figure 8:
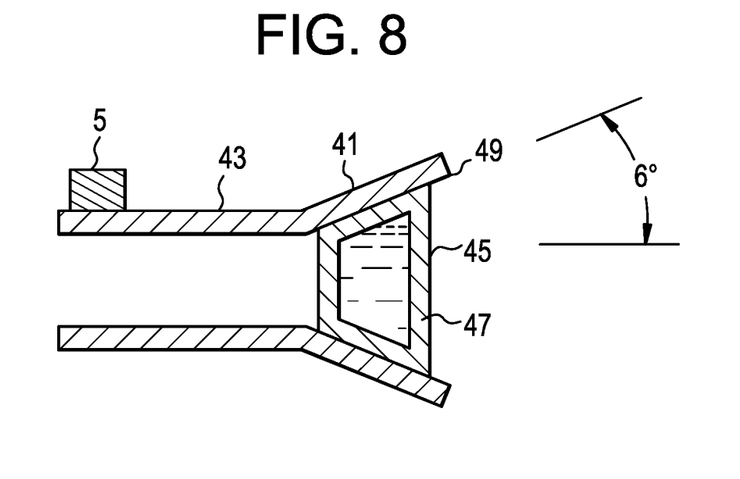
FIG. 8 is a cross-section of a device of the present invention in which a thermally conductive container containing a cooling element forms a Morse taper lock with the base.

Preferably, and now referring to FIG. 8, a proximal portion 41 of the base 43 is in the form of a tube having a 6 degree conical taper expanding proximally, and the container 45 is a frustocone having a matching 6 degree taper expanding proximally, so that they form a Morse taper lock when the container is inserted into the proximal end 49 of the tube. Preferably, the proximal end 47 of the container is recessed below the surface of the proximal end 49 of the tube when the Morse taper lock occurs, thereby preventing its removal. Preferably, a bottom surface 35 of the container 31 has a concave curvature that matches the convex outer curvature of the base 1.

Figure 9:
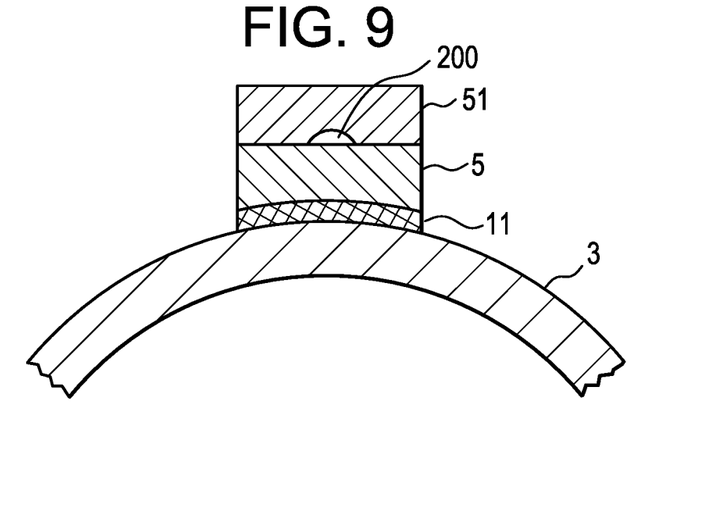
FIG. 9 is a cross section of a device of the present invention in which an optically transparent thermal insulator is placed atop the NIR LED of the light emitter.

Preferably, and now referring to FIG. 9, the light emitter 5 is attached the convex side of the substantially concavo-convex distal end portion by an interlayer comprising double-sided thermally conductive tape 11, or a braze or metallic paste. Preferably, the tape is also electrically resistive.

In some embodiments, the base can be a substantially tubular component adapted to fit between the eye and the eyesocket. Typically, it has a diameter of between 25 and 35 mm. In other embodiments, the base is a portion of tube, typically extending in an arc of at least 90 degrees, preferably at least 120 degrees. Preferably it is made of a metallic material such as aluminum in order to effectively dissipate heat.

The power source can be at least one or a plurality of batteries whose combined voltage output is adequate to drive the plurality of light emitters. The plurality of light emitters are put in electrical connection with the plurality of batteries. Typically, the power source includes conventional electronics such as an on-off switch, a timer, and a constant-current element.

Now referring to FIG. 9, in some embodiments wherein the light emitter 5 is oriented so that a majority of the light emitted by the light emitter faces away from the substantially concavo-convex distal end portion, an optically translucent (preferably substantially optically transparent) thermal insulator 51 is placed over the LED of the light emitter. This insulator has the effect of reducing the heat flux to the eyelid generated by the LED while substantially preserving light transmission from the LED. Preferably the optically translucent thermal insulator comprises a polymer, such as acrylic or polyethylene. More preferably, the polymer is in the form of a foam. The voids in the foam enhance the thermal insulating qualities of the polymer, thereby making it a more effective thermal insulator. In some embodiments, the insulator has a thermal conductivity of no more than 0.030 W/M K, preferably no more than 0.025 W/M K, no more than 0.020 W/M K, no more than 0.015 W/M K. In some embodiments, the translucent thermal insulator is an aerogel, preferably a substantially optically transparent aerogel. In some embodiments in which the thermal insulator is a foam, a transverse hole is provided in the center of the foam to allow light an unobstructed path from the LED to the skin. The thickness of the insulator having the hole is sufficiently thick such that the LED does not contact the skin through the hole in use. In some embodiments in which the translucent thermal insulator is a substantially optically transparent aerogel, there is no transverse hole through the insulator. In some embodiments, the light emitter is attached to a heat pipe by a thermally conductive tape and is oriented so that a majority of the light emitted by the LED faces away from the heat pipe, and an optically translucent (preferably substantially optically transparent) thermal insulator 51 is placed over the LED.

In some embodiments, the power source intermittent provides energy to the LEDs. In some embodiments, the power source comprises an alternating current (AC). In others, the power source comprises a direct current (DC) modified to resemble a square wave with a duty cycle between about 10% and 90%. Preferably the duty cycle is between 25% and 75%. In each of these cases, it is believed that the intermittent energy delivery gives the light emitter time to dissipate heat build up, thereby lowering the maximum temperature at the light emitter. See Bozkurt, *Biomedical Engineering Online*, 2004, 3,9.

Figure 10A:
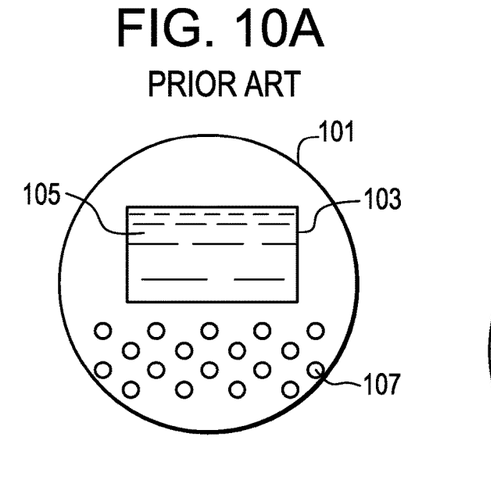
FIG. 10A is a cross-section of a conventional freeze pack bag containing water and an endothermic solute.

Now referring to FIG. 10a, in some embodiments, cooling is achieved by application of instant ice pack technology, in which a large outer bag 101 contains a smaller bag 103 of water 105 and an endothermic reactant 107 that cools when mixed with water, often to temperatures at or below 0° C. In some embodiments, the endothermic reactant is ammonium nitrate while in others it is urea. In some embodiments, the large outer bag is placed in contact with the base and then squeezed so as to rupture the water-containing inner bag. The resulting endothermic reaction between the water and endothermic reactant cools the bag and the base with which it is in contact. The cooled base should also cool the light emitter.

Figure 10B:
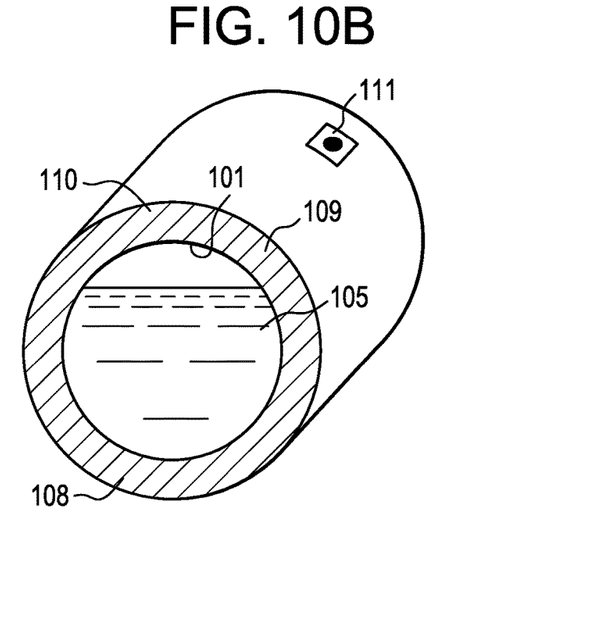
FIG. 10B is a cross-section of a device of the present invention containing a cooling element within the tube that forms the base.

Now referring to FIG. 10b, if the outer bag 101 is placed within the tube 109 after the smaller bag is ruptured, however, the liquid water 105 will seek its lowest resting place and contact only the lowest portion 108 of the tube and not the uppermost portion 110 of the tube where the light emitter 111 resides. This is problematic because the coolant is far away from the light emitter.

Figure 10C:
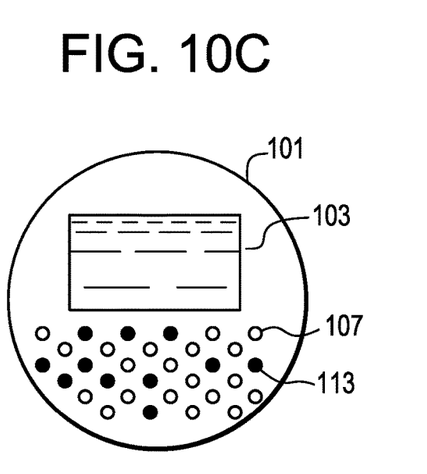
FIG. 10C is a cross-section of a freeze pack bag containing water, an endothermic solute and a gelling agent.
Figure 10D:
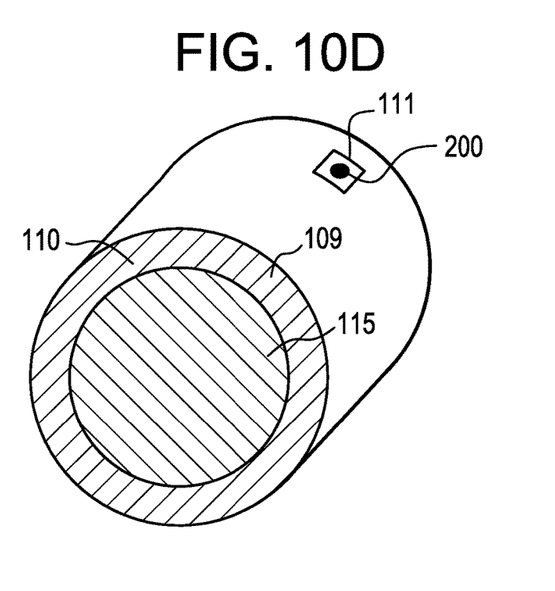
FIG. 10D is a cross section of the device of the present invention in which the cooling element is a gel.

Thus, in some embodiments, and now referring to FIGS. 10c and 10d, the outer bag 101 has a cylindrical shape, the base 109 has a tubular shape, and the outer bag is sized to fit within the tube, wherein the outer bag also contains a gelling agent 113 such as sodium polyacrylate, which gels and expands upon contact with water. Upon squeezing, the gelation and expansion of the sodium polyacrylate acts to completely fill the outer bag with gel 115 such that the entire perimeter of the cylindrical outer bag mates with the inner diameter of the tubular base, thereby providing an intimate cooling surface about its periphery, including the upper region 110 of the tube where the light emitter 111 is located.

Figure 10E:
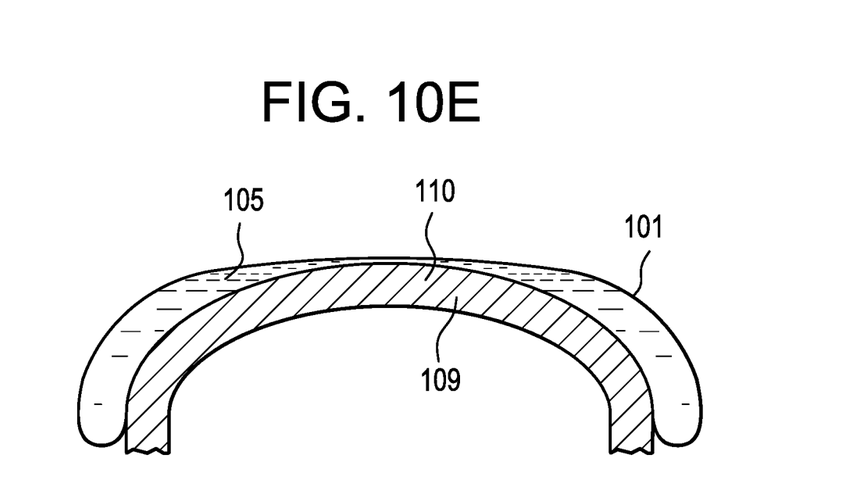
FIG. 10E is a cross-section of the device of the present invention in which the coolant agent is in the liquid state.
Figure 10F:
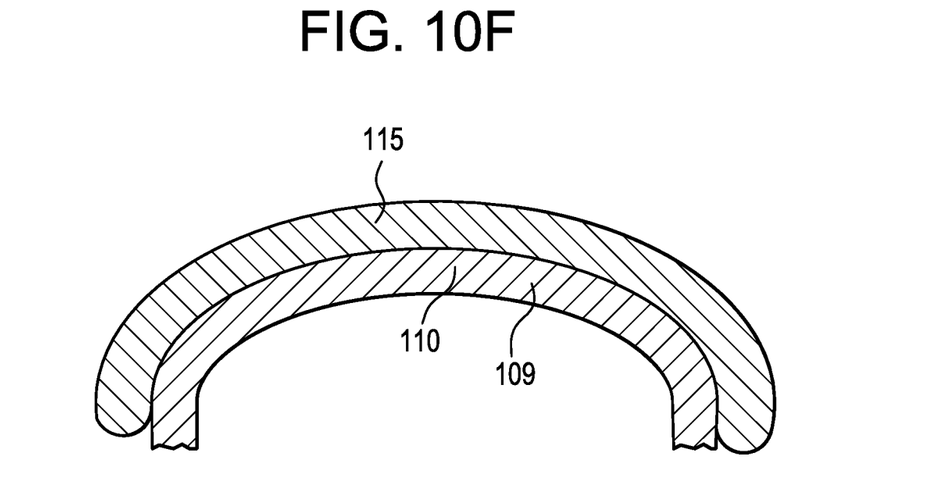
FIG. 10F is a cross-section of the device of the present invention in which the coolant agent is in the gelled state.
Figure 11A:
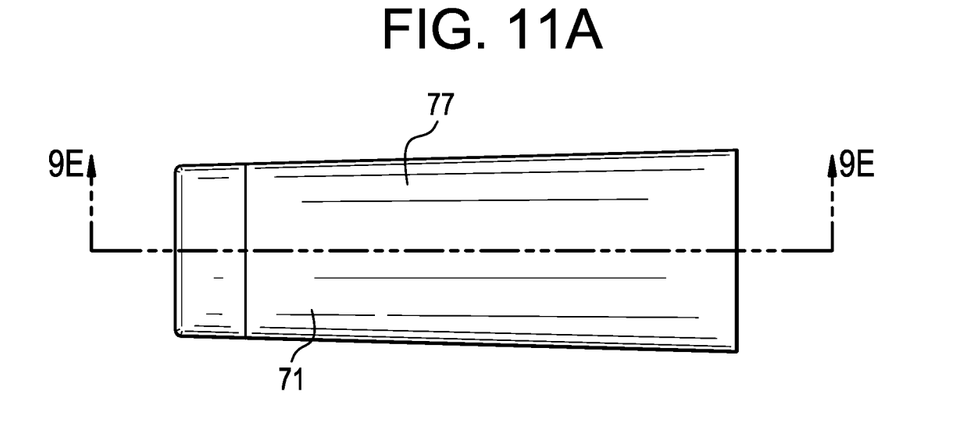
FIGS. 11A-G are various views of a light of the present invention.
Figure 11B:
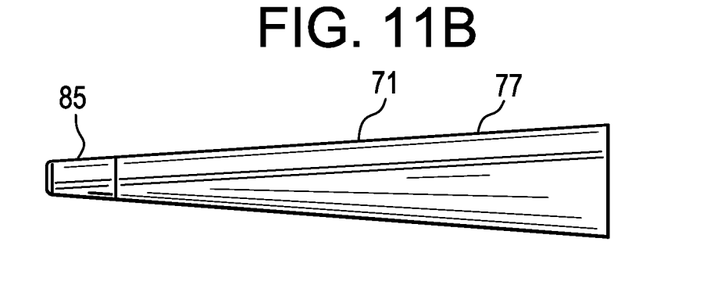
Figure 11C:
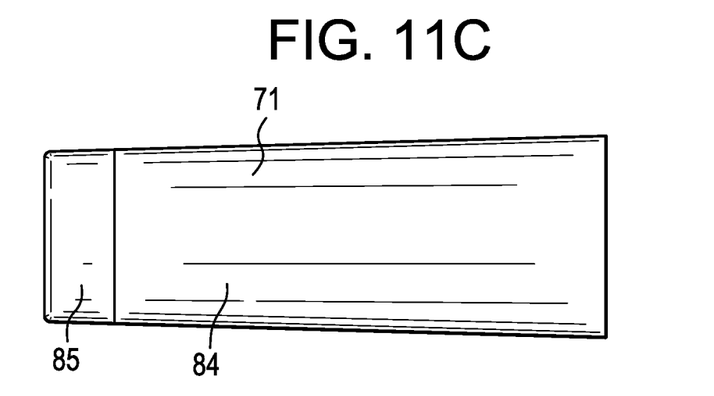
Figure 11D:
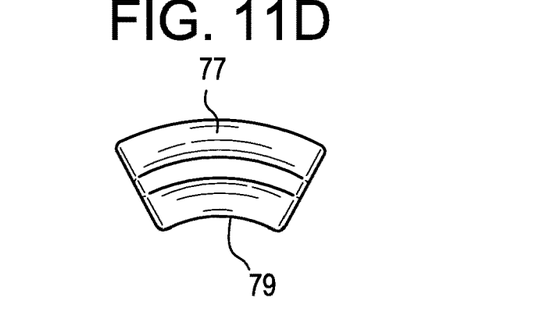
Figure 11E:
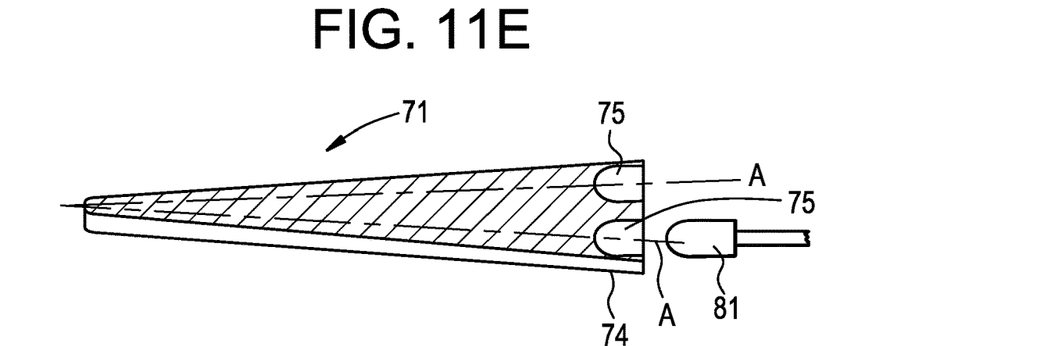
Figure 11F:
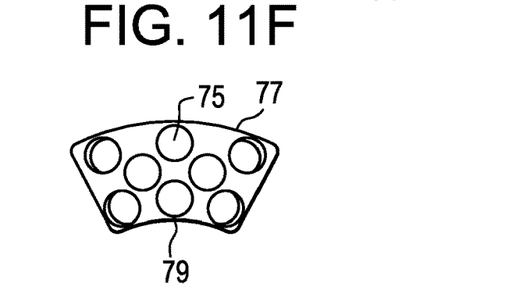
Figure 11G:
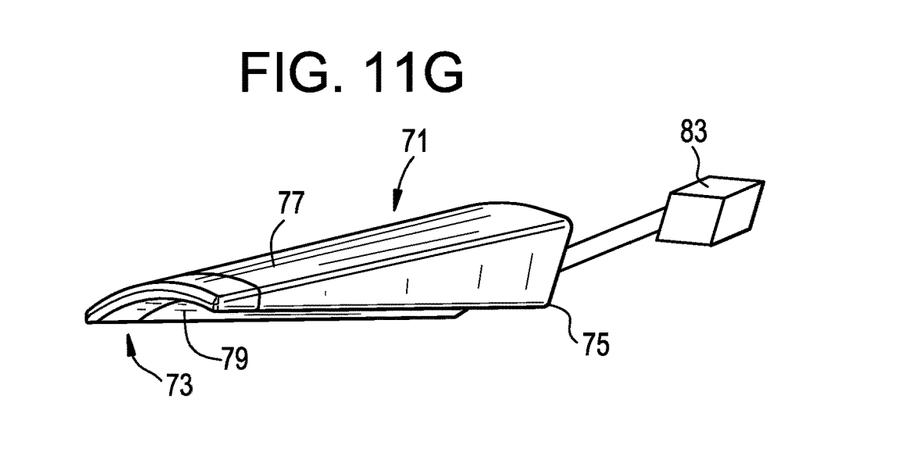

Now referring to FIG. 10e, if the outer bag contains only water and the endothermal coolant but not the sodium polyacrylate and that outer bag is placed upon the tube 109 (instead of in the tube), the liquid water 105 in the bag will seek its lowest resting place and contact only the lowest portion of the bag and not the uppermost portion 110 of the tube where the light emitter resides. Thus, in some embodiments, as in FIG. 10F, the outer bag is substantially flat and is placed upon the upper surface of the base. Again, the outer bag also contains a gelling agent such as sodium polyacrylate, which gels upon contact with water, and the gel 115 expands. The expansion of the sodium polyacrylate acts to completely fill the outer bag such that substantially all of the upper surface of the base has the coolant mixture directly above it. The provides for closer approach of the coolant to the light emitter that resides at the apex of the tube.

When the LED of the light emitter is situated proximate the eyelid, there is a concern with resistive heating from the p-n junction of the LED causing overheating of the eyelid skin. Thus, in some embodiments, the light emitter is moved proximally off the eyelid and a lightpipe is interposed between the light emitter and the eyelid, wherein the lightpipe carries light from the LED to the eyelid. Thus, any heating caused by the LED is carried out a safe distance away from the eyelid.

In some embodiments, and now referring to FIGS. 11a-11g, there is provided a light delivery device comprising:
  a) a light pipe 71 comprising i) a substantially concavo-convex distal end portion 73 adapted to be inserted in a region between the eye and the eyesocket, and ii) a proximal end portion 74 having at least one recess 75 adapted to receive at least one light emitter (preferably a plurality of light emitters); iii) an upper surface 77 and iv) a lower surface 79, wherein the concave portion thereof is displayed on the lower surface and the convex portion thereof is displayed on the upper surface;
  b) at least one light emitter 81 received in the proximal end portion of the light pipe, the light emitters oriented to shine in the distal (posterior) direction;
  c) a power source 83 (preferably at least one battery) electrically connected to the at least one light emitter;
  d) a metallic coating 84 covering the outer surface of the light pipe, and
  e) a light window 85 defined by an absence of metallic coating upon an upper surface of the a substantially concavo-convex distal end portion a substantially concavo-convex distal end portion.

Thus, preferably, the substantially concavo-convex distal end has a thickness of less than 5 mm, preferably less than 3 mm, more preferably less than 2 mm. These relatively thin sections allow for fairly comfortable distal (posterior) insertion of the element into the region between the eye and the eyesocket to a distance of at least 10 mm, preferably at least 15 mm, more preferably at least 20 mm. Likewise, the substantially concavo-convex distal end section preferably has a thickness of less than 5 mm (preferably less than 3 mm) at a distance about 20 mm from the distal end, thereby keeping relatively thin the substantial majority of the light pipe that enters the eyesocket.

Preferably, the light emitters are situated at least 30 mm, preferably at least 50 mm and more preferably at least 70 mm away from the distal end of the lightpipe. In this condition, any heat they generate will not affect the eyelid.

In some embodiments, the proximal end portion of the light pipe comprises recesses 75 adapted to receive light emitters. In some embodiments, the recesses are shaped as substantial cylinders in order to accommodate the conventional substantially cylindrical light emitter. In some embodiments, the recesses are shaped as substantial hemispheres in order to accommodate the conventional substantially hemispherical light emitter. In some embodiments, the light emitter recesses (and hence the light emitters themselves) are each defined by an axis that substantially intersects the distal wall of the substantially concavo-convex distal end portion, thereby pointing the light emitters substantially at the window. In some embodiments, the light emitter recesses are each defined by an axis A that substantially intersects the window, thereby pointing the light emitters directly at the window. In some embodiments, recesses that are on the upper surface are pointed at the lower surface at an angle that allows for the single reflection of light off the lower surface and into the window on the opposite upper surface. Likewise, in embodiments comprising a linear array of light emitters spanning the medial-lateral aspect of the eye, the axes of the light emitter recesses (and hence the light emitters themselves) all substantially point directed forward so that there is a substantially equal distribution of light in the medial-lateral span.

Preferably the window 85 is situated at least 3 mm from the proximal end of the substantially concavo-convex distal end portion, thereby preventing a straight light path from the device to the eye.

In some embodiments, the upper and lower surfaces of the light pipe are polished in order to better reflect incident light.

In some embodiments, the light emitters are selected to be the Vishay VSLY 5850 850 nm light emitter, which are advertised to have a very narrow emission beam (appearing to be around 10 degrees). This light saber nature of this light emitter allows targeting of the window and thus a large portion of the light emitted by these light emitters to travel directly to the window area without having been continually reflected off an upper or lower surface. Thus, in some embodiments, a majority of the light emitted by the light emitter is emitted in a 10 degree cone. In other embodiments, a majority of the light emitted by the light emitter is emitted in a 20 degree cone.

In other embodiments, the light emitters associated with the light pipe are 50 W or 10 W light emitters having an array of 850 nm LEDs, and are available from Hontiey at hontieychina.aliexpress.com In some embodiments, the light pipe is made of a substantially unitary piece of substantially NIR-transparent plastic, such as an acrylic. Typically, the unitary piece is solid. In some embodiments, however, the light pipe can be hollow with reflective material on the inside surface thereof. In these embodiments, the light pipe can be a hollow unitary piece of metal, or a hollow unitary piece of one material (such as plastic) whose inner surface is coated by a reflective surface (such as a metallic coating).

In some embodiments, the distal wall of the light pipe is coated with a metallic material. When this feature is combined with a window that only starts 3-5 mm inward of the distal wall, there is a measure of safety in that light emanating from the window does not have a direct path to the eye, but rather must take a more circuitous route and thereby become subject to the severe attenuation afforded by transmission through tissue.

In other embodiments, the distal wall of the light pipe is uncoated and the window on the upper surface extends to the distal wall. In this condition, the light emanating from the light emitters is afforded an unobstructed path through the distal portion of the light pipe towards the orbitofrontal cortex.

In some embodiments, the light emitters and power source of the embodiment above elements b and c) are provided in the form of a flashlight, and the light pipe can be considered at be an adapter.

In some embodiments, heat pipes are used to transport heat away from the operating light emitters. Heat pipes are generally hollow tubes containing a fully enclosed evaporative fluid that evaporates near a heat source at a first end of the tube, is transported away from the heat source and rejects heat upon condensation at the opposite end of the tube. The cooled liquid is then transported back to the heat source end of the tube by wicking. Heat pipes are typically used in order to provide cooling to an environment.

Figure 12:
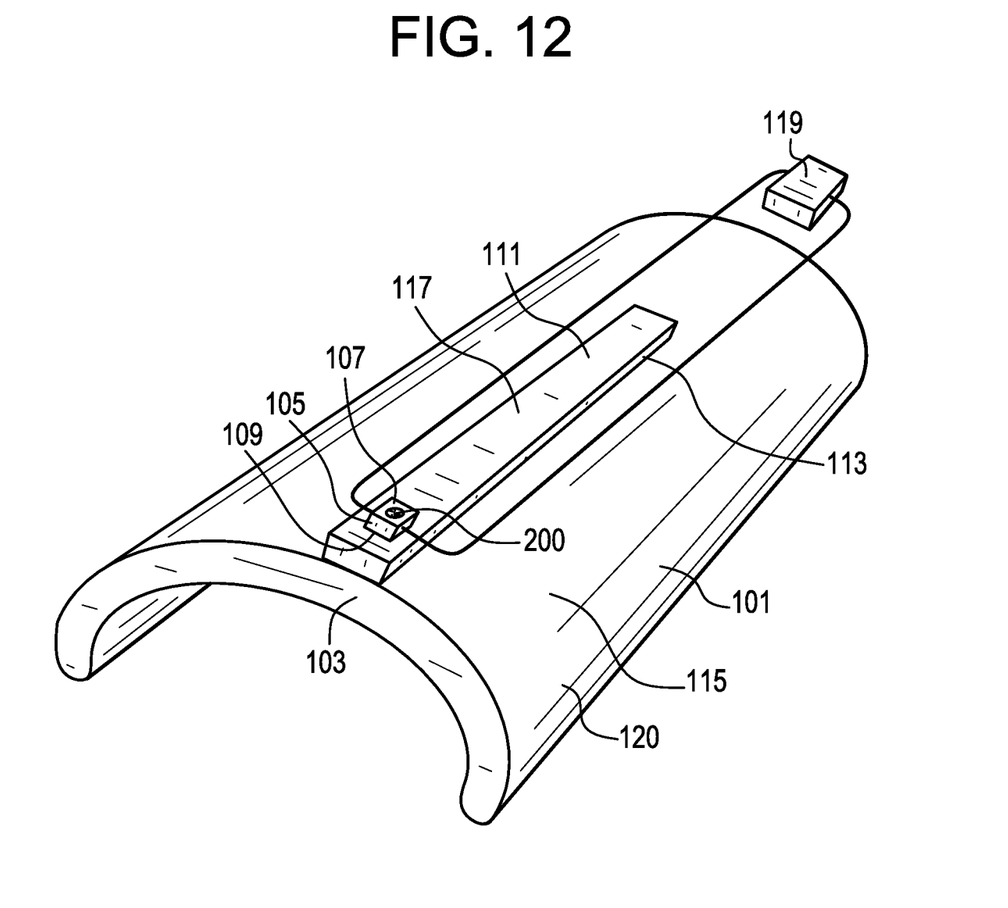
FIG. 12 is a perspective view of an embodiment of the present invention containing a heat pipe.

In some embodiments, and now referring to FIG. 12, there is provided a light delivery device comprising:
a) a base 101 comprising a substantially concavo-convex distal end portion 103,
b) a light emitter 105 having a first light emitting face 107 and a second opposite face 109, and an NIR LED 200 on the first light emitting face,
c) a heat pipe 111 having a first side 113 attached to the convex side 115 of the substantially concavo-convex distal end portion and a second side 117 attached to the second face of the light emitter,
d) a power source 119 in electrical connection with the light emitter,
wherein the light emitter is located in the distalmost quarter 120 of the base.

Figure 13:
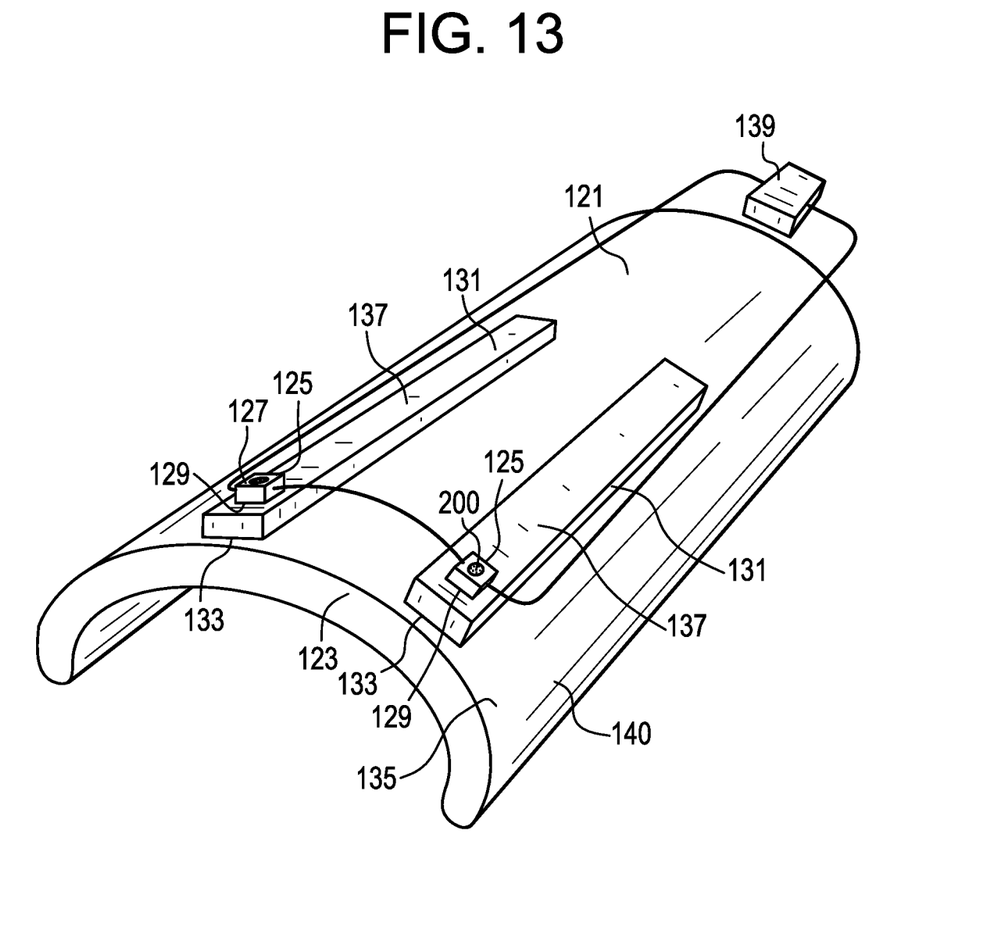
FIG. 13 is a perspective view of an embodiment of the present invention containing a plurality of heat pipes.

In some embodiments, and now referring to FIG. 13, there is provided a light delivery device comprising:
e) a base 121 comprising a substantially concavo-convex distal end portion 123,
f) a plurality of light emitters 125, each light emitter having a first light emitting face 127 and a second opposite face 129,
g) a plurality of heat pipes 131, each heat pipe having a first side 133 attached to the convex side 135 of the substantially concavo-convex distal end portion and a second opposite side 137 attached to the respective second faces of the plurality of light emitters,
h) a power source 139 in electrical connection with the plurality of light emitters.
wherein the light emitters are located in the distalmost quarter 140 of the base.

Figure 14:
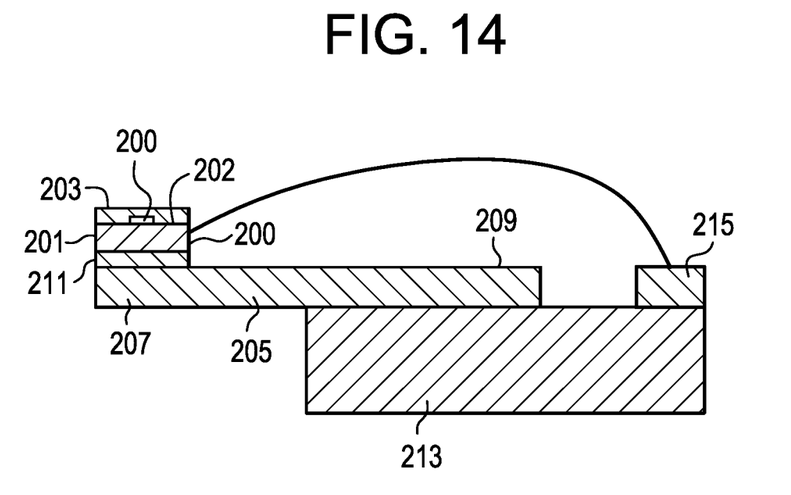
FIG. 14 is a cross-section of an embodiment of the present invention containing an insulator, a heat pipe and a cooling element.

In some embodiments, and now referring to FIG. 14, the NIR light emitting device of the present invention comprises:
a) an NIR light emitter 201 having a lower side 200, an upper side 202, and an NIR LED 200 on the upper side, wherein NIR light is emitted only from the upper side,
b) a substantially NIR-transparent insulator 203 (such as an optically transparent aerogel), c) a heat pipe 205 having a distal end portion 207 and a proximal end portion 209,
d) a cooling element 213, and
e) a power source 215,
wherein the distal end portion of the heat pipe is attached to the lower side of the NIR light emitter (preferably, by double sided, thermally conductive adhesive tape 211),
wherein the substantially transparent insulator is attached to the upper side of the NIR light emitter,
wherein the proximal end of the heat pipe is attached to the cooling element, and
wherein the light emitter is in electrical connection with the power source.

In some embodiments based upon FIG. 14, the insulator is removed. In some embodiments based upon FIG. 14, the cooling element is removed.

Figure 15:
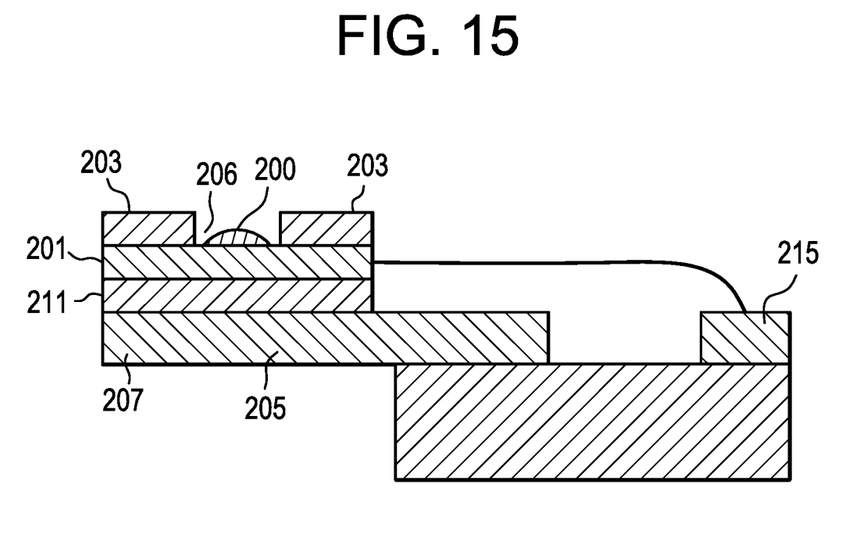
FIG. 15 is a cross-section of an embodiment of the present invention containing an insulator having a hole above the LED.

In some embodiments, and now referring to FIG. 15, the NIR light emitting device of the present invention comprises:
a) an NIR light emitter 201 having a lower side 200 and an upper side 202, and an NIR LED 200 on its upper side,
b) a thermal insulator 203 (such as a styrofoam) having a central vertical throughhole 206,
c) a heat pipe 205 having a distal end portion 207 and a proximal end portion 209,
d) a cooling element 213, and
e) a power source 215,
wherein the distal end portion of the heat pipe and the lower side of the light emitter are attached (preferably, by double side thermally conductive adhesive tape 211),
wherein the thermal insulator is attached to the upper side of the NIR light emitter so that the through-hole is directly above the LED,
wherein the light emitter is in electrical connection with the power source.

In some embodiments based upon FIG. 15, the insulator is removed. In some embodiments based upon FIG. 15, the cooling element is removed.

Therefore, in some embodiments, there is provided an NIR light emitting device comprising:
a) an NIR light emitter having a base having a lower side and an upper side, and an NIR LED attached to the upper side of the base,
b) a thermal insulator,
c) a heat pipe having a distal end portion and a proximal end portion,
d) a cooling element, and
e) a power source,
wherein the distal end portion of the heat pipe is attached to the lower side of the base of the NIR light emitter,
wherein the thermal insulator is attached to the upper side of the base of the NIR light emitter,
wherein the proximal end of the heat pipe is attached to the cooling element,
wherein the NIR light emitter is in electrical connection with the power source.

Figure 16:
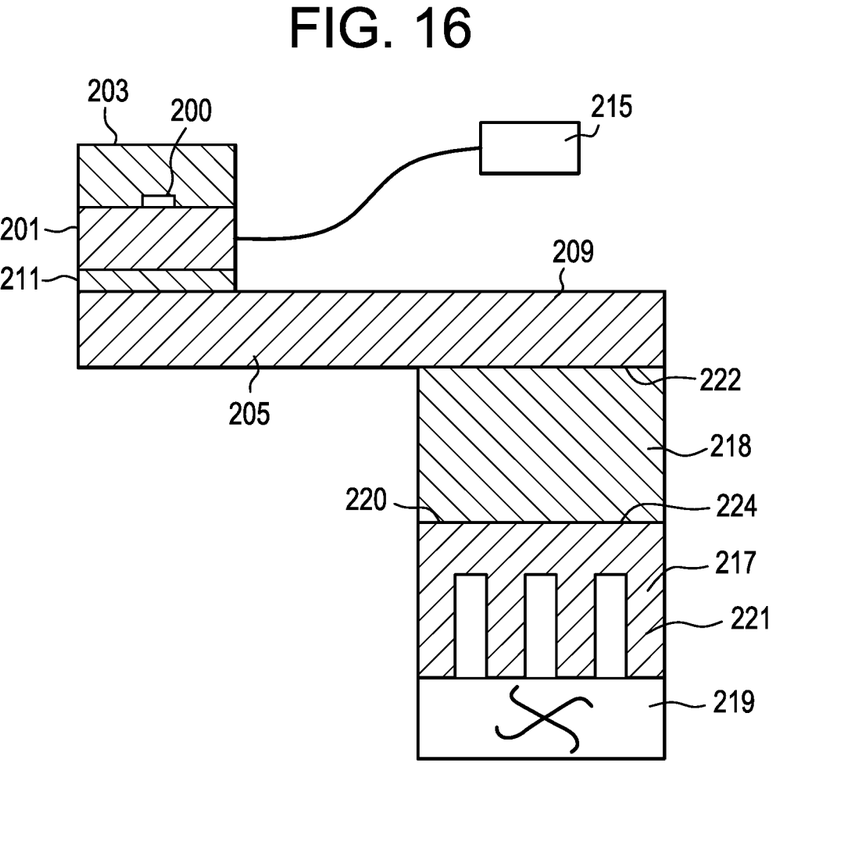
FIG. 16 is a cross-section of an embodiment of the present invention containing a thermoelectric unit, a heat sink and a fan.

In some embodiments, the cooling element comprises an ice pack or endothermic freeze pack. In other embodiments, as in FIG. 16, the cooling element comprises a peltier thermoelectric element 218 having a cool side 222 and a hot side 224, with the cool side 222 being attached to the proximal end portion 209 of the heat pipe. In some embodiments thereof, the hot side of the peltier element is attached to a first side 220 of a heat sink 217, which preferably comprises fins 221. In some embodiments, the fins are attached to a fan 219. Preferably, the peltier thermoelectric element is in electrical connection with a second power source. The fan may be in electrical connection with a third power source. In other embodiments, the cooling element comprises phase-change technology which induces cooling as a result of a phase change of a material in the cooling element. In some embodiments, the phase-change technology is encompassed by embodiments disclosed in U.S. Pat. Nos. 6,559,096; 6,688,132; 6,701,724; 6,968,711, the specifications of which are incorporated by reference in their entireties, and in the Nanocool products of Nanopore, Albuquerque, N. Mex., USA.

In some embodiments, the cooling element contacts the heat pipe in only the proximalmost third of the heat pipe. In some embodiments, the cooling element contacts the heat pipe in only the proximalmost half of the heat pipe. In some embodiments, the cooling element contacts the heat pipe in only the proximalmost two-thirds of the heat pipe. In some embodiments, the cooling element contacts the heat pipe upon substantially all but the distal most 20 mm of the heat pipe. In some embodiments, the cooling element contacts the heat pipe upon substantially all but the distal most one third of the heat pipe. In some embodiments, the cooling element contacts the heat pipe upon substantially all but the distal most one quarter of the heat pipe. In some embodiments, the cooling element contacts the heat pipe upon substantially all but the distal most one fifth of the heat pipe.

Preferably, the insulator that sits above the light emitter has a thermal conductivity of no more than 0.04 W/mK, more preferably no more than 0.03 W/mK, most preferably no more than 0.02 W/mK. In some embodiments, the insulator comprises an expanded polymer material, such as expanded polystryrene. In some embodiments, the insulator has a porosity of at least 95%, preferably at least 98%. In some embodiments, the insulator has a thickness of no more than 4 mm, preferably no more than 3 mm, more preferably no more than about 2 mm. In some embodiments, the length and width of the insulator is substantially the same as that of the light emitter it covers. In some embodiments, the insulator comprises an aerogel. In some aerogel embodiments, the base material is silica, while in others, it is a polymer. In some embodiments, the aerogel is substantially NIR transparent. In some embodiments thereof, one transparent aerogel is available from Aspen Aerogels, Inc. of Northboro, Mass., USA. In some embodiments, the transparent polymer aerogel is selected from embodiments of US 2019-0106543, the specification of which is incorporated by reference in its entirety.

In some heat pipe embodiments, the power source is a 9 Volt DC battery. In some embodiments, a lithium-based 9V battery is used to provide a more stable, longer lasting power input. In other embodiments, the power source comprises alternating current, and in some embodiments thereof includes an AC/AC adaptor that preferably delivers energy in the form of 6V, 1 amp alternating current.

In some embodiments, electronics are included between the power source and light emitter to better manage the energy emitting by the battery or AC current. In some embodiments, the electronics includes a current driver that produces a constant non-degrading current from the DC battery. In some embodiments, the electronics includes current-limiting resistors designed to lower the current across the light emitter. In some embodiments, the electronics include a voltage splitter to lower the voltage across the light emitter while maintaining current. In some embodiments, an Arduino Uno timer is included as part of the electronics to initiate, time and end the light emitter irradiation. In some embodiments, a temperature sensor (Arduino Uno) is used to monitor the temperature of the light emitter. In some embodiments, an optoisolator is used to safeguard and protect the Arduino from possible power surges from the power source. In some embodiments, the optoisolator is connected to the current driver to keep the current stable and minimize temperature and current fluctuations. In some embodiments, the current driver is in series with a resistor and the light emitter in order to provide a desirable 500 mAmp, which was thought to be a desirable tradeoff amperage for producing light intensity while minimizing temperature increase. In some embodiments, a failsafe is coded into the Aruino to cut off power if the temperature of the light emitter reaches a certain maximum temperature.

In some embodiments, the electronics combined with the power source produces a voltage across the LED of about 3.2 volts and an amperage of about 0.45-0.5 amps.

The heat pipes of the present invention are typically hollow tubes with closed ends and a small amount of water under reduced pressure provided in the hollow bore. The inner surface of the heat pipe facing the bore possesses a wicking feature that can be grooved, mesh or sintered. In use, the water in the heat pipe is vaporized by heat flowing from the energized light emitter, where it travels to the cool end of the heat pipe as vapor. At the cool end, heat is rejected from the heat pipe, thereby resulting in condensation of the water vapor. The condensed liquid then travels back to the hot end of the heat pipe via the wicking structure, where the cycle is repeated. Preferably, the heat pipe has a length of between 100 mm and 250 mm; a width of between about 5 and 50 mm, and a height of between 1 mm and 5 mm. The 1 mm height heat pipe has the advantage that its profile can be easily fit into the space between the eyeball and eyesocket, but has a disadvantage in that it produces a relatively low heat flux. In contrast, the 5 mm height heat pipe has the disadvantage that its profile does not easily fit into the space between the eyeball and eyesocket, but has the advantage of producing a relatively high heat flux. In some embodiments, the heat pipe has a width to height ratio of at least 5:1. In some embodiments, the heat pipe has a width to height ratio of no more than 2:1. The very wide heat pipes have the advantage of carrying more than one light emitter, but they should be bent to accommodate the curvature of the eyesocket in widths greater than about 10 mm. In some embodiments, the heat pipe is copper-based while in others, it is aluminum-based. In some embodiments, the heat pipe uses water as its heat flux fluid, while in other it uses acetone. As shorter heat pipes appear to transport more heat more quickly, in some embodiments, the length of the heat pipe is no more than 200 mm, preferably no more than 150 mm, more preferably no more than about 100 mm. In some embodiments, flat heat pipes from Wakefield-Vette of Pelham, N.H., USA are used.

Figure 17:
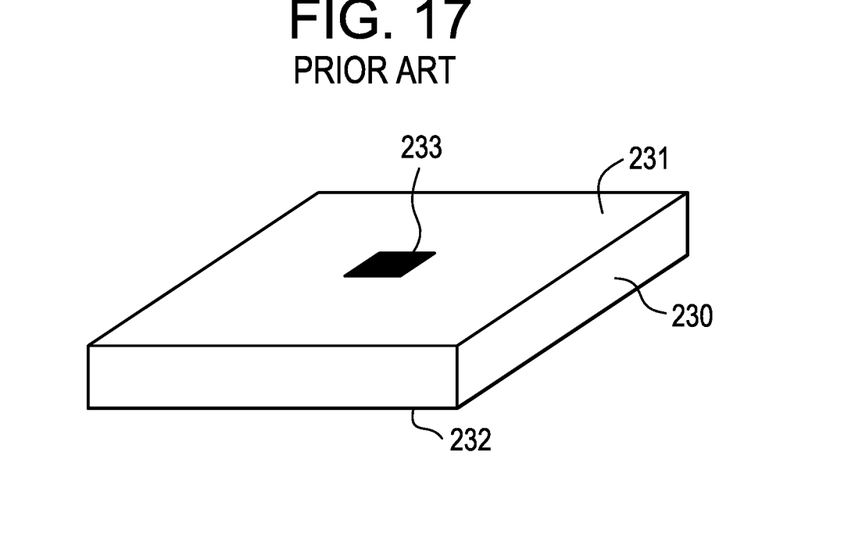
FIG. 17 is a conventional light emitter.

In some heat pipe embodiments, and now referring to FIG. 17, the light emitter comprises a base 230 having an upper side 231, a lower side 232, and an NIR light emitting diode (LED) 233 attached to the upper side of the base. Preferably, the dimensions of the light emitter include a height of no more than 2 mm (preferably no more than about 1 mm); a width of no more than about 10 mm (preferably no more than about 5 mm), and a length of no more than about 10 mm (preferably no more than 5 mm). In some of these embodiments, the light emitter is a Luxeon Saber Micro-Z1 850 nm light emitter, available from Quadica Developments Inc., Brantford, Ontario, CANADA. Preferably, the light emitter has a radiant power of at least about 800 mwatts, preferably at least 900 mwatts, and more preferably at least about 1000 mwatts at 1000 mamp. Preferably, the LED sits in the center of the base and has a width and length of about 1 mm.

In use, the device of the present invention is actuated to cause irradiation from the light emitter and the distal end of the device is pressed upon the eyelid into the space between the eyeball and the top of the eyesocket. In some embodiments, the heat pipe is held at an angle to the ground with the condenser end up, so as to take advantage of the heated vapor's tendency to rise and the condensed liquid's tendency to fall. Therapy is preferably carried out for between about 15 and 30 minutes. US 2018-0193664 (Janssen) is incorporated by reference in its entirety.

I claim:

1. A near infrared light emitting device comprising:
   a) a near infrared light emitter having a base having a lower side and an upper side, and a near infrared LED attached to the upper side of the base,
   b) a thermal insulator,
   c) a heat pipe having a distal end portion and a proximal end portion,
   d) a cooling element, and
   e) a power source,
   wherein the distal end portion of the heat pipe is attached to the lower side of the base of the near infrared light emitter,
   wherein the thermal insulator is attached to the upper side of the base of the near infrared light emitter,
   wherein the proximal end of the heat pipe is attached to the cooling element,
   wherein the near infrared light emitter is in electrical connection with the power source.

2. The device of claim 1 wherein the insulator is a substantially NIR transparent aerogel.

3. The device of claim 1 wherein the cooling element induces cooling as a result of a phase change of a material in the cooling element.

4. The device of claim 1 wherein the heat pipe has a width to height ratio of at least 5:1.

5. The device of claim 1 wherein the length of the heat pipe is no more than 200 mm.

6. The device of claim 1 wherein the heat pipe is made of copper.

7. The device of claim 1 wherein the NIR light emitter has a height of no more than about 1 mm.

8. The device of claim 1 wherein the NIR light emitter has a width of no more than about 5 mm, and a length of no more than about 5 mm.

9. The device of claim 1 wherein the NIR light emitter has a radiant power of at least about 1000 mwatts at 1000 mamps.

* * * * *